United States Patent

Marumoto et al.

[11] 4,225,591
[45] Sep. 30, 1980

[54] 2,6-DIAMINONEBULARINES

[75] Inventors: Ryuji Marumoto, Minoo; Masao Tanabe, Ibaraki; Yoshiyasu Furukawa, Toyonaka, all of Japan

[73] Assignee: Takeda Chemical Industries, Ltd., Osaka, Japan

[21] Appl. No.: 953,254

[22] Filed: Oct. 20, 1978

[30] Foreign Application Priority Data

Oct. 21, 1977 [JP] Japan ................ 52-127148

[51] Int. Cl.³ .................. A61K 31/70; C07H 17/00
[52] U.S. Cl. ........................... 424/180; 536/24
[58] Field of Search ..................... 536/24; 424/180

[56] References Cited

U.S. PATENT DOCUMENTS 3,544,554 1/1970 Koch et al. ............................. 536/26
3,936,439 2/1976 Marimoto et al. ..................... 536/24

FOREIGN PATENT DOCUMENTS 4210518 7/1967 Japan .

Primary Examiner—Johnnie R. Brown
Assistant Examiner—Blondel Hazel
Attorney, Agent, or Firm—Wenderoth, Lind & Ponack

[57] ABSTRACT

Novel N²-substituted phenyl-2,6-diaminonebularines of the formula

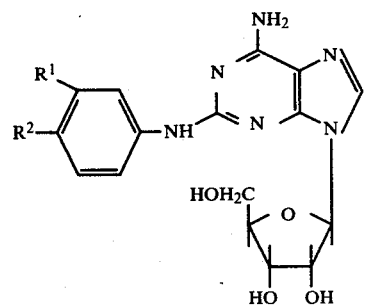

wherein $R^1$ is halogen, lower alkyl or lower alkoxy and $R^2$ is hydrogen, halogen, lower alkyl or lower alkoxy, and their acid addition salts have excellent coronary vasodilator action.

7 Claims, No Drawings

2,6-DIAMINONEBULARINES

The present invention relates to novel $N^2$-substituted phenyl-2,6-diaminonebularines having excellent pharmacological action. More particularly, this invention relates to compounds of the formula

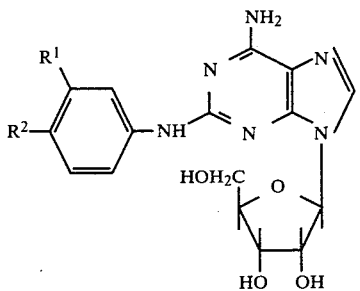

wherein $R^1$ is halogen, lower alkyl or lower alkoxy and $R^2$ is hydrogen, halogen, lower alkyl or lower alkoxy, or their acid addition salts, which have an excellent coronary vasodilator action.

It is described in U.S. Pat. No. 3,936,439 that compounds of the general formula

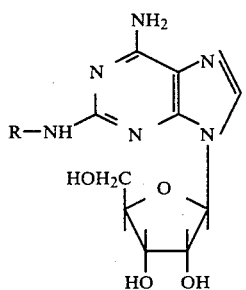

wherein R is a phenyl or cyclohexyl group which may be substituted by halogen, lower alkyl or lower alkoxy and their acid addition salts are of use as coronary vasodilators and platelet aggregation inhibitors.

The present inventors unexpectedly found that in the scope of the $N^2$-substituted phenyl-2,6-diaminonebularines belonging to the formula (II), meta-substituted phenyl compounds among mono-substituted phenyl compounds, and meta- and para-di-substituted phenyl compounds among di-substituted phenyl compounds, have specifically stronger coronary vasodilator action than corresponding compounds substituted in other positions. These $N^2$-(meta-mono-substituted or meta- and para-di-substituted phenyl)-2,6-diaminonebularines are naturally encompassed by the formula (II) but not described concretely in the above-mentioned U.S. Patent. The said new finding was followed by further studies, which have resulted in the present invention.

Thus, the principal object of the present invention is to provide the novel compounds (I) and their acid addition salts which show excellent coronary vasodilator action, and another object is to provide a pharmaceutical composition comprising one or more of these compounds. Other objects will be made clear from the description and claims presented hereinafter.

Referring to the formula (I), the halogen for $R^1$ or $R^2$ may be example be chlorine, bromine or fluorine. The lower alkyl as $R^1$, $R^2$ may be straight-chain or branched and may for example be methyl, ethyl, propyl, isopropyl, n-butyl, t-butyl or hexyl. The lower alkyls of up to 4 carbon atoms are particularly advantageous. The lower alkoxy for $R^1$, $R^2$ may be straight-chain or branched and may for example be methoxy, ethoxy, propoxy, isopropoxy, n-butoxy, t-butoxy or hexoxy. The lower alkoxys of up to 4 carbon atoms are particularly preferred. The substituents $R^1$ and $R^2$ may be the same or different from each other.

The compounds (I) and salts thereof can be produced by, for example, any of the following Processes A, B and C.

Process A

A 2-halogenoadenosine is reacted with an amine of the formula

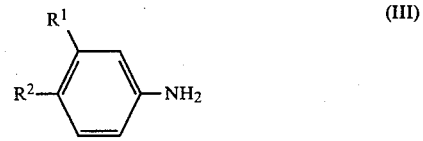

wherein $R^1$ and $R^2$ have the same meanings as respectively defined hereinbefore to yield compound (I).

The 2-halogenoadenosine may for example be 2-fluoroadenosine, 2-chloroadenosine or 2-bromoadenosine.

This reaction may be carried out using about 1 to 10 moles of amine (III) to each mole of 2-halogenoadenosine. The reaction proceeds fast enough at elevated temperatures, from about 50° to 200° C. and, particularly, from about 110° to 150° C. The reaction may optionally be conducted in an inert organic solvent such as methyl-cellosolve or dioxane and, also, optionally in the presence of an acid acceptor such as an alkali metal or alkaline earth metal hydroxide (e.g. sodium hydroxide, potassium hydroxide, lithium hydroxide, calcium hydroxide, barium hydroxide, etc.), an alkali metal or alkaline earth metal carbonate (e.g. sodium hydrogen carbonate, sodium carbonate, potassium carbonate, calcium carbonate, barium carbonate, etc.), organic acid salts of alkali metals or alkaline earth metals (e.g. sodium acetate, potassium acetate, etc.) (Refer to U.S. Pat. No. 3,936,439).

Process B

A compound of the formula

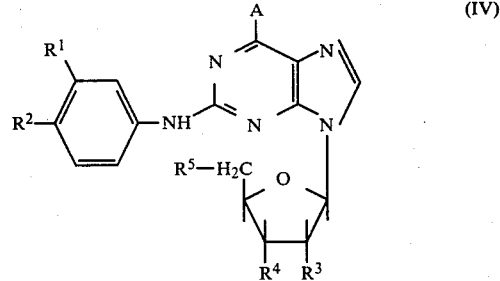

wherein $R^1$ and $R^2$ have the same meaning as defined hereinbefore; $R^3$, $R^4$ and $R^5$ each represents a hydroxyl group which may be protected and A is a reactive group which is able to react with ammonia to yield an amino group, is reacted with ammonia. If necessary, the reaction product is further subjected to a treatment for removal of the protective groups. In this manner, compound (I) is obtained.

Referring to the above formula (IV), the protective groups for hydroxyls $R^3$, $R^4$ and $R^5$ may for example be carboxylic acid-derived acyl groups which may be aliphatic, aromatic, heterocyclic, saturated or unsaturated (e.g. acetyl, propionyl, caproyl, palmitoyl, benzoyl, toluoyl, furoyl, etc.); nitro; sulfonyl; isopropylidene; alkoxyalkylidene and so forth. Particularly advantageous are those acyl groups derived from aliphatic or aromatic carboxylic acids containing up to 7 carbon atoms.

$R^3$, $R^4$ and $R^5$ may all be protected hydroxyls or only some of them, e.g. $R^3$ and $R^4$, may be protected. Or, $R^3$, $R^4$ and $R^5$ may all be unprotected hydroxyls.

These hydroxyl-protecting groups normally detach themselves as the compound (IV) undergoes reaction with ammonia. However, in respect of those protective groups which are not ready to be detached in the course of said reaction with ammonia, such as benzoyl, toluoyl, nitro, sulfonyl, isopropylidene, etc., they may be easily removed by procedures known per se, for example by treatment with an alkali metal alkoxide in the case of benzoyl or toluoyl, by catalytic reduction in the case of nitro, or by treatment with an acid (e.g. formic acid, acetic acid or hydrochloric acid) in the case of isopropylidene.

To reactive group A may be any group that is able to react with ammonia to give an amino group. Thus, for example, it may conveniently be halogen such as chlorine, bromine or iodine, or a group of the formula $-SO_nR^{10}$ (where $R^{10}$ is hydrogen, alkyl or aralkyl; n is 0, 1 or 2) such as mercapto, alkylmercapto, aralkylmercapto, alkylsulfine, alkylsulfone, etc.

In reacting the compound of the formula (IV) with ammonia in Process B, it is generally preferable to dissolve ammonia in a solvent and to use it in an amount not less than equimolar, preferably about 2 to 3 molar equivalents with respect to compound (IV). The solvent may for example be a lower alcohol (e.g. methanol or ethanol), methylcellosolve or water or a mixture thereof. Generally this reaction proceeds satisfactorily at an elevated temperature of about 100° to 200° C. and it is particularly desirable to heat the reaction system to the above-mentioned temperature in a gas-tight reactor. The starting compound (IV) can be prepared by the procedure disclosed in U.S. Pat. No. 3,936,439 mentioned hereinbefore or a modification thereof.

Process C

A compound of the formula

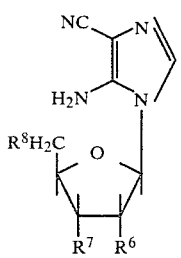 (V)

wherein $R^6$, $R^7$ and $R^8$ each is a hydroxyl group which may be protected is reacted with a compound of the formula

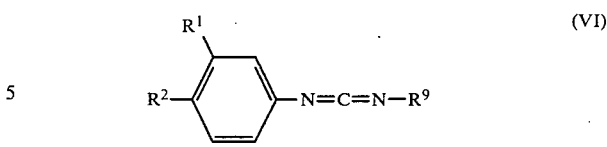 (VI)

wherein $R^1$ and $R^2$ each has the same meaning as defined hereinbefore and $R^9$ is hydrogen or a group of the formula

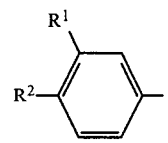

and the reaction product is subjected, if necessary, to a de-protecting treatment to obtain a compound (I).

Referring to the above formula (V), protective groups for the protected hydroxyls $R^6$, $R^7$ and $R^8$ may be any of the groups mentioned in connection with $R^3$, $R^4$ and $R^5$, propionyl being the most advantageous. $R^6$, $R^7$ and $R^8$ may all be protected hydroxyls or only some of them, e.g. $R^6$ and $R^7$, may be protected. Or all of $R^6$, $R^7$ and $R^8$ may be free hydroxyl groups. Although these hydroxyl-protecting groups generally detach themselves as compound (V) undergoes reaction with compound (VI), they can be easily removed by procedures known per se, for example by treatment with a base (aqueous ammonia or alkali metal alkoxide) in the case of carboxylic acid-derived acyl groups, by catalytic reduction in the case of nitro, or by treatment with an acid (e.g., formic acid, acetic or hydrochloric acid) in the case of isopropylidene.

Referring to the formula (VI), $R^9$ means either hydrogen or a group represented by

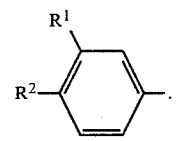

Thus, this formula encompasses both cyanamides and carbodiimides. These cyanamides can be easily prepared, for example by the procedure described in Berichte der Deutschen Chemischen Gesellschaft 18, 3217-3234(1885) or a modification thereof, while the carbodiimides can be easily prepared, for example by the procedure described in Journal of Organic Chemistry 32, 2895(1967) or a modification thereof.

In reacting compound (V) with compound (VI) in Process C, it is generally desirable to employ at least an equimolar amount, preferably about 2 to 5 molar equivalents, of compound (VI) with respect to compound (V). Generally, this reaction is preferably conducted in the presence of a base. The base may for example be ammonia, a primary to tertiary amine (which is preferably a low-boiling amine, inclusive of a cyclic amine, e.g. n-propylamine, isopropylamine, n-butylamine, triethylamine, pyridine, picoline, 2,6-lutidine, etc.), a sodium or potassium alkoxide (e.g. sodium methoxide, sodium ethoxide, sodium methoxyethoxide, potassium tert.-butoxide, etc.) or the like, ammonia being the most advantageous. Normally such a base is preferably used in a proportion of about 10 to 100 molar equivalents with respect to compound (V). Generally this reaction is desirably conducted in a solvent. The solvent may be any organic solvent that will not interfere with the contemplated reaction. Thus, for example, lower alkanols (e.g. methanol, ethanol, propanol, etc.), tetrahydrofuran, dioxane or dimethylformamide, as well as mixtures thereof, may be advantageously employed. Generally this reaction proceeds satisfactorily at elevated temperatures of about 100° to 200° C., and is preferably conducted in a gas-tight reactor.

When the resultant product compound still carries protective groups on its hydroxyl functions, such protective groups can be easily removed by a de-protecting treatment which has hereinbefore been described. By the above procedure there is obtained a compound of the formula (I).

The above-mentioned starting compound (V) may, for instance, be produced in good yield from 5-amino-1-β-D-ribofuranosylimidazole-4-carboxamide, which is a readily available, inexpensive fermentation product, in two or three steps by the method disclosed in U.S. Pat. No. 3,450,693 or a modification thereof.

The $N^2$-substituted phenyl-2,6-diaminonebularine (I) thus produced can be easily separated from the reaction mixture by procedures known per se. For example, the excess reactants and solvent are first distilled off from the reaction mixture and the residue is washed with a lower alkanol or the like and recrystallized from water or a lower alkanol or a mixture thereof, whereby compound (I) is obtained in pure form. This compound (I) can also be isolated in the form of a physiologically acceptable acid addition salt i.e. inorganic acid salt (e.g. hydrochloride, sulfate, nitrate or phosphate) or organic acid salt (e.g. acetate, propionate, citrate or tartrate) by treatments known per se.

The $N^2$-substituted phenyl-2,6-diaminonebularines (I) and salts thereof, which are provided by this invention, are novel compounds which have not been described in any literature reference and have excellent coronary vasodilator action, besides being low in toxicity. Therefore, these compounds are of value as drugs for the treatment of ischemic heart diseases such as coronary insufficiency, angina pectoris, myocardial infarction and the like in mammalian animals (e.g. man; pet animals such as dog and cat, and laboratory animals such as rat and mouse). When the compound of this invention is used for such medicinal purposes, it can be orally or parenterally administered as such or in combination with appropriate pharmaceutically acceptable carriers, vehicles or diluents, in such dosage forms as powders, granules, tablets, capsules, injections, etc. While the proper dosage depends on such factors as, for example, the disease to be managed and the route of administration, coronary insufficiency in an adult human, for instance may be effectively treated with about 3 to 30 mg./day by the oral route or about 0.1 to 2.0 mg./day by the intravenous route.

The following Examples, Reference Example and Experiment are intended to further illustrate this invention and should by no means be construed as limiting the scope of the invention.

Throughout the foregoing description as well as in the following Examples, Reference Example, Experiment and Claims, "μg.", "mg.", "g.", "kg.", "ml.", "l.", "°C", "N" and "M" respectively refer to "microgram(s)", "milligram(s)", "gram(s)", "kilogram(s)", "milliliter(s)", "liter(s)", "degree(s) centigrade", "Normal(s)" and "Molar concentration".

REFERENCE EXAMPLE

In 500 ml. of methanol was suspended 100 g. of m-chloroaniline and, following addition of 100 ml. of concentrated hydrochloric acid, the mixture was concentrated to dryness under reduced pressure. The hydrochloride thus obtained was dissolved in 500 ml. of water, and with the addition of 110 g. of potassium thiocyanate, the solution was heated at 90° C. for 3 hours, whereupon crystals (60 g.) of m-chlorophenylthiourea separated out. The crystals were suspended in 1 l. of 10% aqueous potassium hydroxide and, following addition of 220 g. of lead acetate, the mixture was stirred at room temperature for 20 minutes and at 80° C. for another 20 minutes. The precipitated lead sulfide was filtered off and the filtrate was neutralized with acetic acid. By the above procedure was obtained 30 g. of m-chlorophenylcyanamide as crystals melting at 82°–84° C.

In the same manner as above, the N-substituted phenylcyanamides given in Table 1 were synthesized.

Table 1

| $R^1$ | $R^2$ | Melting point (°C.); Infrared absorption spectrum (KBr) |
|---|---|---|
| CH$_3$— | H— | Oil, 2230cm$^{-1}$(—CN) |
| CH$_3$O— | H— | Oil, 2220cm$^{-1}$(—CN) |
| F— | H— | 57 |
| Br— | H— | 86–87 |
| Cl— | Cl— | 139 |
| CH$_3$— | CH$_3$— | 75–76 |
| Cl— | CH$_3$— | 105–106 |
| CH$_3$O— | CH$_3$O— | 107–109 |
| Cl— | CH$_3$O— | 66–68 |
| n-C$_4$H$_9$— | H— | Oil, 2230cm$^{-1}$(—CN) |

EXAMPLE 1

(1) In a mixture of 350 ml. of pyridine and 400 ml. of propionic anhydride, 258 g. of 5-amino-1-β-D-ribofuranosylimidazole-4-carboxamide was stirred at room temperature for 16 hours. The reaction mixture was concentrated to dryness under reduced pressure and the syrupy residue was diluted with 2.5 l. of water and triturated. The resultant crystals were washed with water and dried. By the above procedure there was obtained 355 g. of 5-amino-1-(2,3,5-tri-O-propionyl-β-D-ribofuranosyl)imidazole-4-carboxamide, m.p. 155°–116° C. A portion of this product was recrystallized from ethanol-diethyl ether to obtain colorless needles melting at 117°–118° C.

| Elemental analysis: | C(%) | H(%) | N(%) |
|---|---|---|---|
| Calculated for C$_{18}$H$_{26}$N$_4$O$_8$: | 50.70 | 6.15 | 13.14 |
| Found: | 50.60 | 6.10 | 13.21 |

(2) In a mixture of 1.12 l. of chloroform and 278 ml. of triethylamine was dissolved 170.4 g. of 5-amino-1-(2,3,5-tri-O-propionyl-β-D-ribofuranosyl)imidazole-4-carboxamide and, under ice-cooling and stirring, a solution of 39.6 ml. of phosphorus oxychloride in 360 ml. of chloroform was added dropwise over a period of 3 hours, the internal temperature being maintained not higher than 10° C. throughout this period. After the dropwise addition had been completed, the mixture was further stirred for 1.5 hours, at the end of which time it was poured in 400 ml. of ice-water. The chloroform layer was taken and washed with 400 ml. of water twice, 400 ml. of 1N-HCl twice and 200 ml. of a saturated aqueous solution of sodium chloride in the order mentioned. The solution was then dried over anhydrous sodium sulfate and concentrated to dryness. By the above procedure there was obtained 149 g. of 5-amino-4-cyano-1-(2,3,5-tri-O-propionyl-$\beta$-D-ribofuranosyl-)imidazole as a syrupy residue.

Nuclear magnetic resonance spectrum (CDCl$_3$) $\delta$(Hz): 1.17 (9H, 3Me), 2.46(6H, 3-CH$_2$—), 4.50(3H, H$_{4',5'}$), 5.20(2H, NH$_2$), 5.30–5.90(3H, H$_{1'}$, $_{2'}$, $_{3'}$), 7.40 (1H, H$_2$).

The above syrup was dissolved in a mixture of 280 ml. of methanol and 280 ml. of 25% aqueous ammonia and the solution was allowed to stand at room temperature for 5 hours. The reaction mixture was concentrated to dryness and the residue was washed with a small amount of methanol. By the above procedure there was obtained 63 g. of 5-amino-1-$\beta$-D-ribofuranosyl-4-cyanoimidazole as pale-yellow needles melting at 206°–208° C.

(3) A mixture of 15 g. of 5-amino-1-$\beta$-D-ribofuranosyl-4-cyanoimidazole and 20 g. of m-chlorophenyl-cyanamide was heated in 150 ml. of 20% methanolic ammonia at 180° C. for 5 hours in an autoclave. The reaction mixture was concentrated to dryness and the residue was washed with 50 ml. of ethanol and recrystallized from 3 l. of 20% aqueous ethanol. By the above procedure there was obtained 4 g. of N$^2$-(m-chlorophenyl)-2,6-diaminonebularine as colorless needles melting at 254°–255° C. (decomposition).

| Elemental analysis: | C(%) | H(%) | N(%) |
|---|---|---|---|
| Calculated for C$_{16}$H$_{17}$O$_4$N$_6$Cl: | 48.92 | 4.36 | 21.39 |
| Found: | 48.73 | 4.52 | 21.58 |

In 800 ml. of 60% ethanol was suspended 8 g. of the above product, and at 80° C., 26 ml. of 1N-HCl was added, whereupon the crystals dissolved. The resultant solution was concentrated to about 600 ml, and, then, allowed to stand and cool. By the above procedure there was obtained 8 g. of N$^2$-(m-chlorophenyl)-2,6-diaminonebularine hydrochloride as colorless needles melting at 188°–190° C.

| Elemental analysis: | C(%) | H(%) | N(%) | Cl(%) |
|---|---|---|---|---|
| Calculated for C$_{16}$H$_{17}$N$_6$O$_4$Cl · HCl · ½H$_2$O: | 43.85 | 4.37 | 19.17 | 16.17 |
| Found: | 43.60 | 4.32 | 19.66 | 16.30 |

EXAMPLE 2

In a manner similar to that of Example 1(3), 3.6 g. of 5-amino-4-cyano-1-(2,3,5-tri-O-acetyl-$\beta$-D-ribofuranosyl)imidazole, 4 g. of m,p-dimethylphenylcyanamide and 20 ml. of 20% methanolic ammonia were reacted and treated to obtain 0.7 g. of N$^2$-(m,p-dimethylphenyl)-2,6-diaminonebularine as crystals melting at 193°–195° C.

| Elemental analysis: | C(%) | H(%) | N(%) |
|---|---|---|---|
| Calculated for C$_{18}$H$_{22}$O$_4$N$_6$: | 55.95 | 5.74 | 21.75 |
| Found: | 55.10 | 5.76 | 21.60 |

EXAMPLE 3

In 40 ml. of pyridine were suspended 26 g. of 5-amino-1-$\beta$-D-ribofuranosylimidazole-4-carboxyamide and 110 g. of benzoic anhydride and the suspension was stirred at 50° C. for 3 hours. The reaction mixture was concentrated and the residue was washed with 300 ml. of diethyl ether and dissolved in a mixture of 200 ml. of chloroform and 50 ml. of triethylamine. Under ice-cooling and stirring, 80 ml. of a chloroform solution containing 8 ml. of phosphorus oxychloride was added dropwise over one hour. After the dropwise addition had been completed, the mixture was stirred under ice-cooling for another 2 hours, at the end of which time it was poured in 100 ml. of ice-water. The chloroform layer was taken, washed with 100 ml. of water twice, 100 ml. of 1N-hydrochloric acid twice and 50 ml. of a saturated aqueous solution of sodium chloride twice and then concentrated to dryness. After addition of diethyl ether, the residue was allowed to stand, whereupon 33 g. of 5-amino-4-cyano-1-(2,3,5-tri-O-benzoyl-$\beta$-D-ribofuranosyl)imidazole was obtained as crystals. A portion of this product was recrystallized from ethanol. The resultant crystals melted at 148°–150° C. Infrared absorption spectrum (KBr): 2230cm$^{-1}$(—CN).

A mixture of 5.5 g. of the above crystals, 8 g. of di(m-chlorophenyl)carbodiimide and 20 ml. of 20% methanolic ammonia was heated at 180° C. for 5 hours in an autoclave, after which time the rection mixture was concentrated to dryness. The residue was dissolved in 60 ml. of 1M-sodium ethoxide and the solution was alloed to stand at room temperature of 20 hours. The reaction mixture was concentrated and, after the addition of 200 ml. of icewater and 100 ml. of ethyl acetate, the mixture was adjusted to pH 2 with 1N-HCl under stirring. The water layer was taken, neutralized and allowed to stand in the cold. By the above procedure there was obtained 0.8 g. of N$^2$-(m-chlorophenyl)-2,6-diaminonebularine as crystals.

EXAMPLE 4

In 200 ml. of methyl-cellosolve, 10 g. of 2-bromoadenosine and 7 ml. of m-anisidine were boiled for 16 hours. The reaction mixture was concentrated to dryness, the residue was washed with diethyl ether and the insolubles were dissolved in methanol and adsorbed on 10 g. of silica gel. This silica gel was placed on top of a column of 500 g. silica gel and elution was carried out with chloroformmethanol (9:1, volume/volume). The fractions rich in the desired compound were pooled and concentrated to dryness. The residue was recrystallized from 20% ethanol. By the above procedure was obtained 1.7 g. of N$^2$-(m-methoxyphenyl)2,6-diaminonebularine as colorless needles melting at 134°–135° C.

| Elemental analysis: | C(%) | H(%) | N(%) |
|---|---|---|---|
| Calculated for C$_{17}$H$_{20}$O$_5$N$_6$: | 52.57 | 5.19 | 21.64 |
| Found: | 51.69 | 5.29 | 21.84 |

EXAMPLE 5

A mixture of 10 g. of 2-bromoinosine ammonium salt, 15 g. of m-toluidine and 120 ml. of 60% aqueous methanol was boiled for 3 hours and the needle-crystals separating out when cold were recovered by filtration. By this procedure was obtained 7.1 g. of 2-(m-methylphenylamino)inosine melting at 220°–222° C. (decomposition). This product was dissolved in 70 ml. of pyridine and following addition of 35 ml. of acetic anhydride, the solution was allowed to stand at room temperature. It was then concentrated to dryness under reduced pressure and the residue was dissolved in 200 ml. of chloroform and dried over anhydrous sodium sulfate. To the chloroform solution were added 6 ml. of dimethylformamide and 6 ml. of phosphorus oxychloride under ice-cooling, followed by boiling for one hour. The reaction mixture was concentrated and the residual oil was decomposed with ice-water and extracted with 300 ml. of ethyl acetate. The extract was washed with water twice and, then, washed with a saturated aqueous solution of sodium hydrogen carbonate and water in the order mentioned. It was then concentrated to dryness to obtain 2-(m-methylphenylamino)-6-chloro-2',30',5'-tri-O-acetylnebularine as an oily residue. This residue was dissolved in 200 ml. of 20% methanolic ammonia and heated in a sealed tube at 130° C. for 5 hours. The reaction mixture was concentrated to dryness and the residue was recrystallized from boiling water. By the above procedure there was obtained 1.2 g. of N²-(m-methylphenyl)-2,6-diaminonebularine as crystals melting at 231°–232° C.

| Elemental analysis: | C(%) | H(%) | N(%) |
|---|---|---|---|
| Calculated for $C_{17}H_{20}O_4N_6$: | 54.83 | 5.41 | 22.57 |
| Found: | 54.30 | 5.45 | 22.39 |

In 100 ml. of 50% ethanol was suspended 3.7 g. of the above product and the suspension was heated to 60° C., followed by addition of 11 ml. of 1N-HCl, whereupon the crystals dissolved. This solution was concentrated to about 70 ml. and allowed to stand and cool. By the above procedure there was obtained 3.5 g. of N²-(m-methylphenyl)-2,6-diaminonebularine hydrochloride as colorless crystals melting at 198°–202° C.(decomposition).

| Elemental analysis: | C(%) | H(%) | N(%) | Cl(%) |
|---|---|---|---|---|
| Calculated for $C_{17}H_{20}N_6O_4$ . HCl . ½$H_2O$: | 48.85 | 5.31 | 20.08 | 8.49 |
| Found: | 48.92 | 5.51 | 20.42 | 8.16 |

EXAMPLES 6–12

The compounds (I) described below in Table 2 were produced by the reaction and purification procedures similar to those set forth in Examples 1 to 5.

Table 2

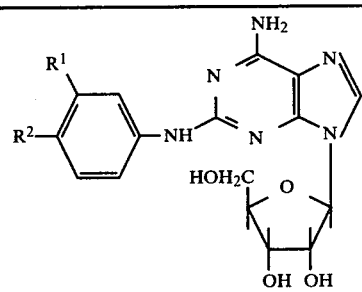

(I)

| Example No. | $R^1$ | $R^2$ | Molecular formula | Elemental analysis* C(%) | H(%) | N(%) | Melting point (°C.) |
|---|---|---|---|---|---|---|---|
| 6 | F— | H— | $C_{16}H_{17}N_6O_4F$ | 51.06<br>50.77 | 4.55<br>4.43 | 22.33<br>22.35 | 262–264** |
| 7 | Br— | H— | $C_{16}H_{17}N_6O_4Br$ | 43.93<br>43.88 | 3.91<br>3.84 | 19.21<br>19.62 | 245–247 |
| 8 | Cl— | $CH_3$— | $C_{17}H_{19}N_6O_4Cl$ | 50.18<br>49.52 | 4.71<br>4.74 | 20.61<br>20.58 | 250–251 |
| 9 | $CH_3O$— | $CH_3O$— | $C_{18}H_{22}N_6O_6$ . ½$H_2O$ | 50.58<br>50.08 | 5.42<br>5.38 | 19.66<br>20.20 | 205–207 |
| 10 | Cl— | $CH_3O$— | $C_{17}H_{29}N_6O_5Cl$ . $H_2O$ | 46.31<br>46.84 | 4.80<br>4.74 | 19.06<br>19.58 | 180–182 |
| 11 | Cl— | Cl— | $C_{16}H_{16}N_6O_4Cl_2$ | 44.98<br>44.80 | 3.78<br>3.60 | 19.67<br>19.87 | 247–248 |
| 12 | $n$-$C_4H_9$— | H— | $C_{20}H_{26}N_6O_4$ | 57.96<br>57.61 | 6.32<br>6.11 | 20.28<br>19.83 | 173 |

*:Calculated in top rows; found in bottom rows.
**:Decomposition point

EXAMPLE 13

For the treatment of ischemic heart diseases such as coronary insufficiency, angina pectoris or myocardial infarction, the compound (I) of the present invention can be administered, for example, in the following formulations:

1. Tablet (1) N²-(m-chlorophenyl)-2,6-diaminonebularine   5 mg.

-continued

| | |
|---|---|
| (2) Lactose | 35 mg. |
| (3) Corn starch | 150 mg. |
| (4) Microcrystalline cellulose | 30 mg. |
| (5) Magnesium stearate | 5 mg. |
| | 225 mg./tablet |

The components (1), (2) and (3), two-thirds of (4) and one-half of (5) are admixed and granulated, followed by the addition of the balance each of (4) and (5). The mixture is compression-molded into a tablet.

2. Capsules

| | |
|---|---|
| (1) $N^2$-(m-methylphenyl)-2,6-diaminonebularine | 5 mg. |
| (2) Lactose | 100 mg. |
| (3) Microcrystalline cellulose | 70 mg. |
| (4) Magnesium stearate | 10 mg. |
| | 185 mg./capsule |

The components (1), (2), (3) and one-half of (4) are admixed and granulated, followed by the addition of the balance of (4). The mixture is sealed into a gelatin capsule.

3. Injectable solution

| | |
|---|---|
| (1) $N^2$-(m-chlorophenyl)-2,6-diaminonebularine hydrochloride | 0.2 mg. |
| (2) Inositol | 100 mg. |
| (3) Benzyl alcohol | 20 mg. |

The components (1), (2) and (3) are dissolved in distilled water for injection to make a total of 2 ml., the solution is sealed into a brown-colored ampoule and the plenum air is purged with nitrogen gas. The entire process is aseptically performed.

EXPERIMENT

Dogs weighing 7 to 12 kg. were anesthetized with sodium pentobarbital (30 mg./kg., intravenous injection) and, under forced respiration, a left thoracotomy was performed at the fifth interspace to expose the heart. The heart was perfused with the blood led from the fermoral artery to the left coronary arterial circumfles through a polyethylene catheter and the coronary blood flow was measured with an electromagnetic flowmeter interposed in the extracorporeal circuit.

The test compound as a 1 μg./ml. solution in physiological saline, was directly administered into the coronary artery via the polyethylene catheter at the dosage of 0.1 μg./dog, and at timed intervals of 30 seconds, one minute, 2 minutes, 3 minutes and 5 minutes after the dosing, the increase in coronary blood flow was measured. The results are set forth in Table 3.

The percent increases in coronary blood flow were computed by means of the following equation $$\frac{\left(\begin{array}{c}\text{Coronary blood flow}\\\text{at each time point}\\\text{after dosing}\end{array}\right) - \left(\begin{array}{c}\text{Coronary blood flow}\\\text{before dosing}\end{array}\right)}{\text{Coronary blood flow before dosing}} \times 100 =$$

Percent increase in coronary blood flow

Table 3

| | Percent increase in coronary blood flow After dosing | | | | |
|---|---|---|---|---|---|
| Compound | 30 seconds | 1 minute | 2 minutes | 3 minutes | 5 minutes |
| $N^2$-(m-chlorophenyl)-2,6-diaminonebularine | 116.0 | 77.7 | 64.7 | 45.0 | 17.9 |
| $N^2$-(m-methylphenyl)-2,6-diaminonebularine | 126.7 | 45.3 | 19.0 | 10.0 | — |
| $N^2$(m-methoxyphenyl)-2,6-diaminonebularine | 44.5 | 26.5 | 15.0 | 7.5 | — |
| $N^2$-(m-fluorophenyl)-2,6-diaminonebularine | 87.0 | 47.7 | 34.7 | 16.3 | 2.0 |
| $N^2$-(m,p-dimethylphenyl)-2,6-diaminonebularine | 85.0 | 30.7 | 13.7 | 8.5 | 3.7 |
| $N^2$-(m-chloro-p-methylphenyl)-2,6-diaminonebularine | 59.0 | 43.0 | 16.0 | 6.5 | — |

What is claimed is:

1. A compound selected from the group consisting of $N^2$-(m-methylphenyl)-2,6-diaminonebularine, $N^2$-(m-methoxyphenyl)-2,6-diaminonebularine, $N^2$-(m-chlorophenyl)-2,6-diaminonebularine, and $N^2$-(m,p-dimethylphenyl)-2,6-diaminonebularine or a pharmaceutically acceptable acid addition salt thereof.

2. A compound according to claim 1, said compound being $N^2$-(m-methylphenyl)-2,6-diaminonebularine.

3. A compound according to claim 1, said compound being $N^2$-(m-methoxyphenyl)-2,6-diaminonebularine.

4. A compound according to claim 1, said compound being $N^2$-(m-chlorophenyl)-2,6-diaminonebularine.

5. A compound according to claim 1, said compound being $N^2$-(m,p-dimethylphenyl)-2,6-diaminonebularine.

6. A compound according to claim 1 wherein the acid addition salt is the hydrochloride.

7. A pharmaceutical composition which comprises, as the active ingredient, a pharmaceutically effective amount of a compound or salt thereof according to claim 1 together with a pharmaceutically acceptable carrier, vehicle or diluent.

* * * * *